United States Patent [19]

Broadhurst et al.

[11] Patent Number: 4,850,371
[45] Date of Patent: Jul. 25, 1989

[54] NOVEL ENDOTRACHEAL TUBE AND MASS SPECTROMETER

[76] Inventors: John H. Broadhurst, 1560 Sumter Ave. North, Golden Valley, Minn. 55427; Marvin B. Bacaner, 4401 Fremont Ave. South, Minneapolis, Minn. 55409

[21] Appl. No.: 205,668

[22] Filed: Jun. 13, 1988

[51] Int. Cl.⁴ .............................................. A61B 5/08
[52] U.S. Cl. ............................ 128/719; 128/207.14; 128/207.15; 604/45
[58] Field of Search ................... 128/207.14, 207.15, 128/719, 720, 725, 730; 604/43, 45, 283; 138/40, 44

[56] References Cited

U.S. PATENT DOCUMENTS

| | | | |
|---|---|---|---|
| 2,862,498 | 12/1958 | Weekes | 128/207.14 |
| 3,896,792 | 7/1975 | Vail et al. | 128/719 |
| 3,927,670 | 12/1975 | Turney et al. | 128/719 |
| 4,022,219 | 5/1977 | Basta | 128/207.14 |
| 4,141,364 | 2/1979 | Schultze | 128/207.15 |
| 4,148,308 | 4/1979 | Sayer | 128/207.14 |
| 4,169,465 | 10/1979 | Walls et al. | 128/719 |
| 4,402,684 | 9/1983 | Jessup | 128/207.14 |
| 4,485,822 | 12/1984 | O'Connor et al. | 128/719 |
| 4,610,663 | 9/1986 | Rosenberg | 604/283 |
| 4,717,379 | 1/1988 | Ekholmer | 604/43 |

Primary Examiner—Charles Pearson
Assistant Examiner—Aaron J. Lewis
Attorney, Agent, or Firm—Herman H. Bains

[57] ABSTRACT

A non-invasive apparatus for continuously measuring the cardiac output and cardio-respiratory function includes a gas sampling device which is inserted into the mouth of a human subject. The gas sampling device may be a disposable endotracheal tube or a smaller disposable mouthpiece. Each of these gas sampling devices is provided with a plurality of passages for sampling the lung gases and for continuously sampling the gas pressure on opposite sides of a capillary restriction member. A miniature motor pump mass spectrometer module is mounted on the upper end of the endotracheal tube or mouthpiece. Electronic circuitry connected to the mass spectrometer permits constant visual monitoring of the cardiac output and cardio-respiratory function.

9 Claims, 4 Drawing Sheets

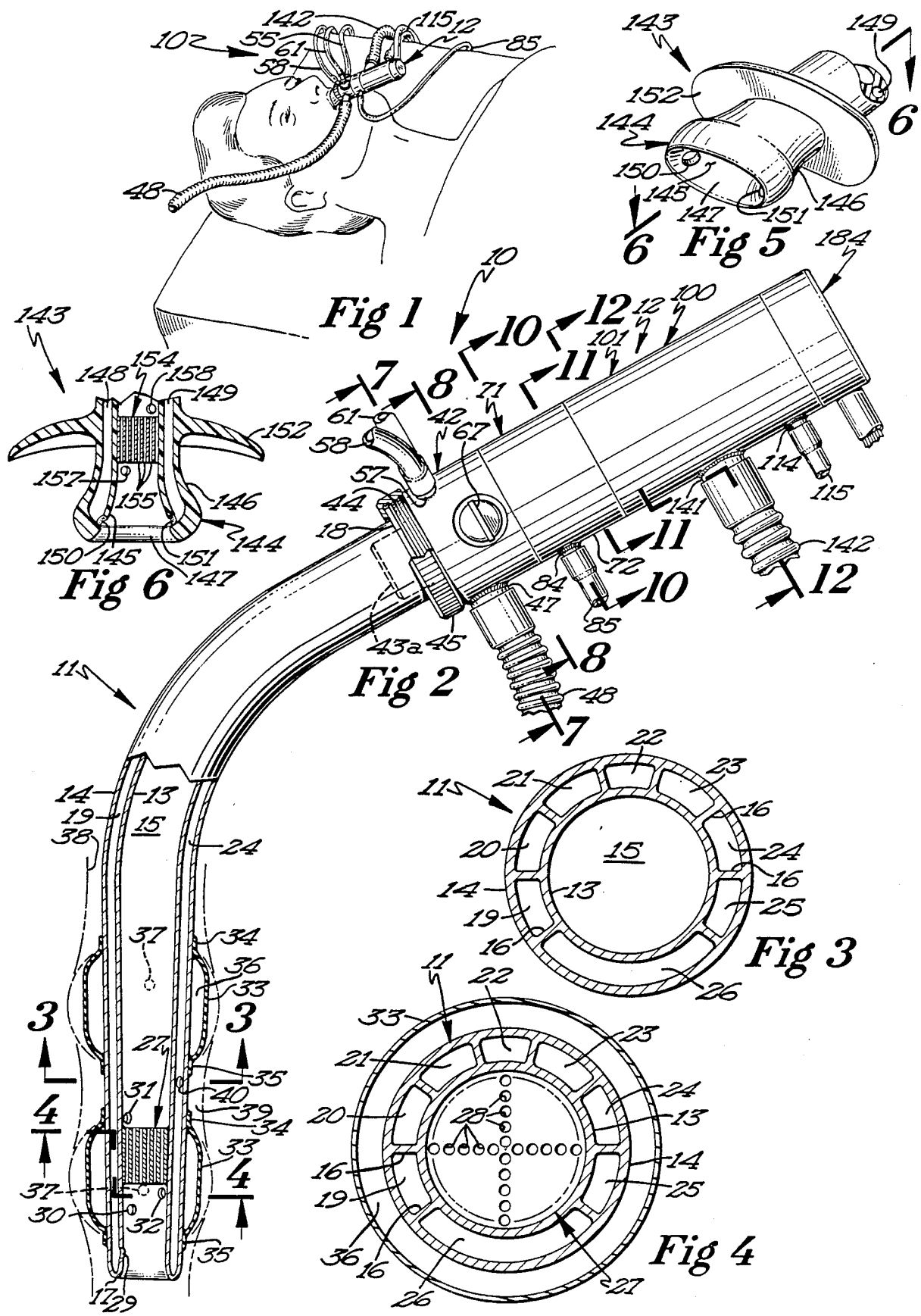

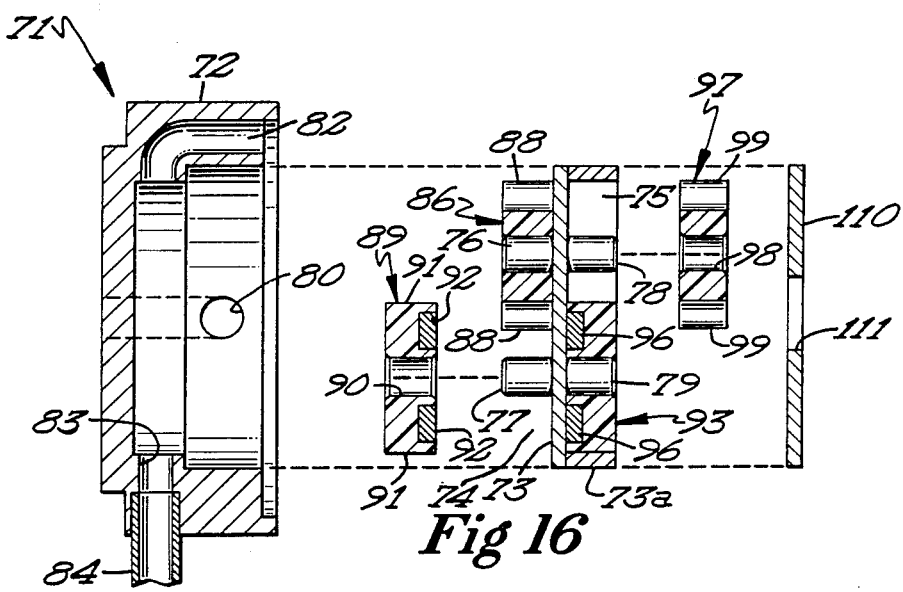
Fig 16
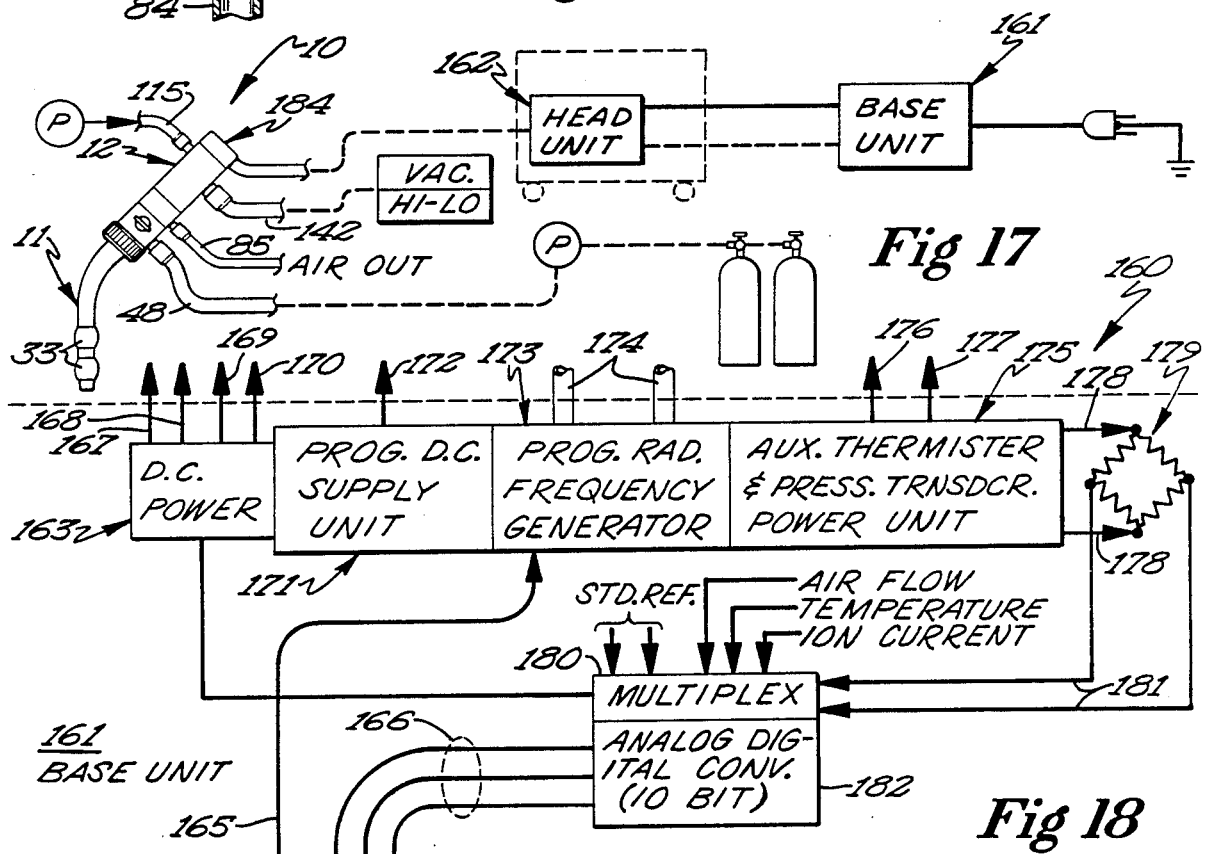
Fig 17
Fig 18

NOVEL ENDOTRACHEAL TUBE AND MASS SPECTROMETER

FIELD OF THE INVENTION

This invention relates to a device which measures the quantity and composition of inhaled and expired gases from a conscious or unconscious human subject and then computes the pulmonary function and cardiac output of the subject from this data information.

BACKGROUND OF THE INVENTION

It is desirable, and often necessary, to determine the cardio-respiratory function in human subjects. The function of the cardio-vascular and respiratory system is to supply oxygenated blood to the body tissues and to remove the $CO_2$ produced by the tissues for excretion by ventilation of the lungs. The amount of blood pumped or vented and the amount of $O_2$ and $CO_2$ in the blood, as well as the volume of lung ventilation, are critical reflections of the adequacy of the circulatory and respiratory function.

During exercise, during disease states, or during surgery, these physiological parameters are adaptively altered and may be impaired. In order to diagnose and treat cardio-respiratory dysfunction, it is necessary to measure and evaluate these parameters. This is particularly true during surgical anesthesia, where the anesthetist must maintain cardio-respiratory homeostasis that may become impaired from the anesthetic agent or from complications during surgery. It is also necessary to assess these parameters in critically ill non-surgical patients while being managed in critical care units. Moreover, assessment of cardiac output and other cardio-respiratory functions, which should be a key part of exercise testing, is not evaluated routinely because there are presently no effective non-invasive methods which are acceptable.

Invasive systems are available, but cannot be routinely used because the insertion procedure (via catheter or the like) is time-consuming and involves risk. Non-invasive devices, such as the ultrasonic Doppler device, have been developed, but cannot be used routinely and are unable to continuously accurately determine the cardio-respiratory function.

SUMMARY OF THE INVENTION

It is an object of the present invention to provide a novel non-invasive device, which continuously measures the quantity and composition of the inhaled and expired gases from a human subject, and then calculates the pulmonary function and cardiac output from this data.

More specifically, it is an object of this invention to provide a non-invasive system for determining the cardio-respiratory function comprised of a specially designed endotracheal tube having a miniature mass spectrometer mounted thereon, which is operable to continuously measure $O_2$, $CO_2$, total volume and temperature of respired air, as well as tissue $PO_2$ and $PCO_2$, and other gases exchanged from the tracheal tissue compartment. It will be appreciated that such measurements provide the data to permit rapid calculation of the cardiac output, as well as a determination of the adequacy of tissue perfusion.

It, therefore, is an object of this invention to provide a novel endotracheal tube and a novel miniature mass spectrometer which cooperate with each other and continuously and rapidly measure the cardio-respiratory function of a human subject.

In carrying out this invention, a specially designed endotracheal tube is provided, which has several auxiliary passages along its length. The ventilation function of the endotracheal tube is not altered, and the sample gases are circulated through the auxiliary passages to the mass spectrometer for quantitative analysis. In the preferred embodiment of the invention, the endotracheal tube is preferably a disposable item and may be readily detached from the mass spectrometer motor pump module.

FIGURES OF THE DRAWING

FIG. 1 is a perspective view of the endotracheal tube and mass spectrometer unit as it is applied to a patient;

FIG. 2 is an enlarged side elevational view of the endotracheal tube and mass spectrometer and motor pump module, with certain parts thereof broken away for clarity;

FIG. 3 is a cross-sectional view taken approximately along the line 3—3 of FIG. 2 and looking in the direction of the arrows;

FIG. 4 is a cross-sectional view taken approximately along the line 4—4 of FIG. 2 and looking in the direction of the arrows;

FIG. 5 is a perspective view illustrating a mouthpiece as an alternative form to the endotracheal tube;

FIG. 6 is a cross-sectional view taken approximately along the line 6—6 of FIG. 2 and looking in the direction of the arrows;

FIG. 16 is a sectional view of the motor pump unit partially exploded to illustrate details of construction thereof, but rotated through an arc of 90 degrees;

FIG. 17 is a diagrammatic view of the invention, showing the major components thereof; and FIG. 18 is a circuit diagram of the circuitry employed to operate the novel system.

DESCRIPTION OF THE PREFERRED EMBODIMENT

Figure 7:
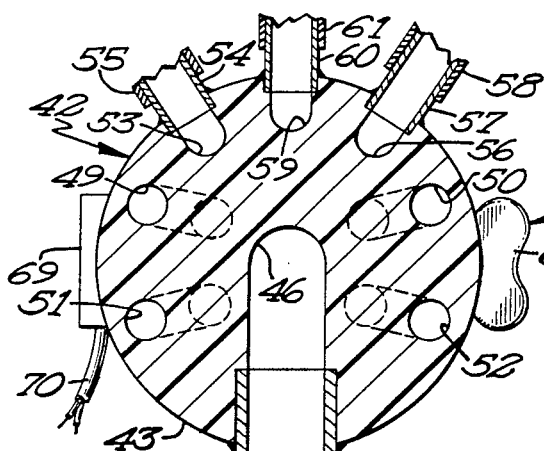
FIG. 7 is a cross-sectional view taken approximately along the line 7—7 of FIG. 2 and looking in the direction of the arrows.
Figure 10:
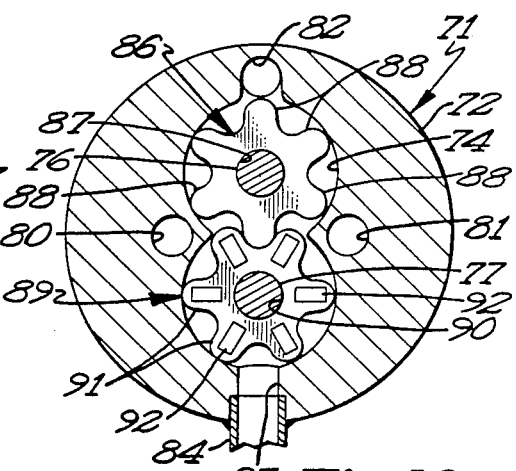
FIG. 10 is a cross-sectional view taken approximately along the line 10—10 of FIG. 2 and looking in the direction of the arrows.

Referring now to the drawings and, more specifically, to FIGS. 1 through 4, it will be seen that one embodiment of the novel endotracheal tube and mass spectrometer apparatus, designated generally by the reference numeral 10, is there shown. The apparatus 10 is comprised of a flexible, preferably disposable, endotracheal tube 11 formed of suitable inert flexible plastic material, which is detachably connected to a motor pump and mass spectrometer module 12. The endotracheal tube 11 is comprised of an inner tube 13 and an outer tube 14. The double wall endotracheal tube 11 may be formed in any conventional manufacturing operation, such as a single-piece extrusion, or the endotracheal tube structure may be assembled from two tubes. The inner tube 13 defines a central passage 15 throughout its length and the central passage serves to ventilate the lungs in the manner of a conventional endotracheal tube.

Figure 15:
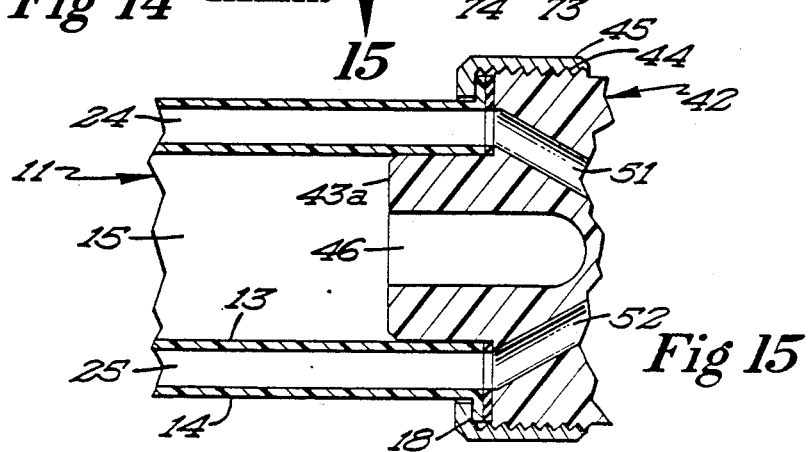
FIG. 15 is a cross-sectional view taken approximately along the line 15—15 of FIG. 14 and looking in the direction of the arrows, but rotated through an arc of 90 degrees.

The inner tube 13 and outer tube 14 are interconnected together by a plurality of elongate interconnecting wall elements 16, which cooperate with the inner and outer tubes to divide the inter-tubular space into a plurality of circumferentially arranged passages. The inner and outer tubes are joined together at their respective lower ends, as at 17, while the upper ends of the inner and outer tubes are provided with and connected to an outturned rigid annular member 18, as best seen in FIG. 15. The interconnecting wall elements 16 divide the inner tubular space into circumferentially arranged passages 19 through 26, respectively. These passages extend throughout the length of the endotracheal tube.

A capillary restriction member 27 is positioned within the inner tube 13 adjacent the lower end 17 of the endotracheal tube and is provided with a plurality of capillaries or passages 28 therethrough. Referring now to FIGS. 2 and 4, it will be seen that the capillaries or passages 28 extend axially through the capillary restriction member 27 so that gases flowing through the passage 15 must pass through the capillaries 28. It will be appreciated that a pressure differential exists on opposite sides or ends of the capillary restriction member 27.

Referring again to FIG. 2, it will be seen that the lower end portion of the endotracheal tube 11 is provided with an opening 29 in the inner tube 13 thereof, which communicates with the passage 19. A second opening 30, located adjacent the opening 29, communicates with the passage 20. Inhaled and expired gases from the human subject pass through the opening 30 into the passage 20 and flow in an upward direction so that passage 20 defines a sample passage. Conversely, a portion of these sample gases is returned through the passage 19 and is discharged through the opening 29 into the lower tracheal area. Therefore, the passage 19 constitutes a return passage, and the gases flow in a downward or return direction.

It will also be noted that the inner tube 13 has an opening 31 therein, located above the capillary restriction member 27, which communicates with the passage 21. An opening 32 in the inner tube 13, located below the capillary restriction member 27, communicates with the passage 23. The passages 21 and 23 are connected to a differential pressure transducer for sensing and analyzing the gaseous pressure located below and above the capillary restriction member to thereby determine the lung volume or capacity.

The outer tube 14 has a pair of flexible sleeve-like members 33 secured thereto adjacent the lower end portion of the endotracheal tube. These flexible sleeve-like members 33 are longitudinally spaced apart, and each has its upper annular edge portion 34 and its lower annular edge sealingly secured to the outer wall. The volumetric space located between each sleeve-like member 33 and the outer tube defines a chamber 36. Thus, each sleeve-like member 33 cooperates with the outer tube 14 to define a pair of inflatable balloons that may be selectively inflated and deflated by the operator.

In this regard, the outer tube 14 has a pair of longitudinally spaced apart openings 37 therein, each communicating with one of the chambers 36. Each opening also communicates with the passage 22, through which air may be passed to inflate each of the respective balloons 33 or to allow the balloons to be deflated. The balloons provide a dual function, one of which is to engage the tracheal wall of the human subject and function as a retaining means. The inflatable balloons 33 also cooperate with the tracheal wall of the human subject to define a tracheal wall sampling cell for measuring tracheal tissue $O_2$ and $CO_2$, which closely reflect arterial $PO_2$ and provide an approximation of arterial $PCO_2$ because the metabolic rate of the trachea is very low.

Referring again to FIG. 2, it will be noted that the sleeve-like members or balloons 33 are illustrated in an inflated condition for engaging the trachea wall 38. These balloons 33 cooperate with the tracheal wall 38 to define a tracheal sampling cell 39 defined by the volumetric space located between the inflated balloons 33, the outer tube 14, and the tracheal wall 38.

It will be seen that the outer tube 14 has an opening 40 therein, which communicates with the passage 24. The outer tube 14 also has an opening 41 therein, which communicates with the passage 25. When the balloons 33 are in the inflated condition, the opening 40 intercommunicates the passage 24 with the tracheal sampling cell 39, while the opening 41 intercommunicates the passage 25 with the tracheal sampling cell. Sample gases from the tracheal cell flow upwardly through the sample passage 24 for analysis by the mass spectrometer, while tracheal sample gases are returned through the return passage 25 to the tracheal sampling cell.

The upper end of the endotracheal tube is detachably connected to the motor pump and mass spectrometer module 12 by means of a manifold unit 42, which constitutes a component of the pump and mass spectrometer module. The manifold unit 42 includes a manifold body 43 having a reduced portion 43a, which projects into the inner tube 13 of the endotracheal tube 11. The manifold body has an external threaded portion 44, which is threadedly engaged by an internally threaded nut 45 having an inturned annular lip 45a. The inturned annular lip 45a engages the rigid annular member 18 secured to the upper end of the endotracheal tube and releasably secures the endotracheal tube to the manifold unit. The rigid annular member 18 has openings therein which are in registry with the respective passages of the endotracheal tube.

The manifold body 43 has an L-shaped passage 46 therethrough, which extends through the reduced portion 43a and communicates with the large ventilating passage 15 of the inner tube 13. The manifold body is provided with a fitting 47 having a flexible hose 48 connected thereto, which is connected to a source of oxygen and anesthesia gas for ventilating the lungs of the human subject in a conventional manner, as best seen in FIG. 17. It will, therefore, be seen that a mixture of oxygen and anesthesia gas is circulated through the passage 46 and into the ventilation passage 15 of the endotracheal tube for circulation to the respiratory system of the human subject when the human subject is anesthetized.

Referring now to FIGS. 7 through 9 and 14 and 15, it will be seen that the manifold body 43 is provided with a passage 49, which communicates with the sample passage 20 of the endotracheal tube 11. The manifold body is also provided with a passage 50, a passage 51, and a passage 52 therein. Passage 50 communicates with the return passage 19 in the endotracheal tube, and passage 51 communicates with the tracheal sample passage 24 of the endotracheal tube. Passage 52 in the manifold body communicates with the passage 25 of the endotracheal tube and returns tracheal tissue sample gases to the tracheal sampling cell 39.

The manifold body 43 is also provided with passages 53, 59, and 56 therein, as best seen in FIG. 7. Passage 53 communicates with passage 21 of the endotracheal tube and passage 56 communicates with passage 23 therein Passage 59 communicates with passage 22 in the endotracheal tube, through which air under pressure passes to inflate or deflate the balloons 33.

It will be seen that the gas pressure from the zone located below and above the capillary restriction member 27, respectively, passes through the passages 53 and 56 to a differential pressure transducer where the lung capacity or volume is determined. In this regard, the passage 53 is provided with a fitting 54 having a hose 55 attached thereto which, in turn, is connected to the differential pressure transducer. Similarly, the passage 56 is provided with a fitting 57 having a hose 58 connected thereto, which is also connected in communicating relation with the pressure transducer. Finally, the passage 59 is provided with a fitting 60 having a hose 61 connected thereto, which is connected to a suitable small pump or similar pressure producing device, which is operable for inflating and deflating the balloons 33.

Figure 8:
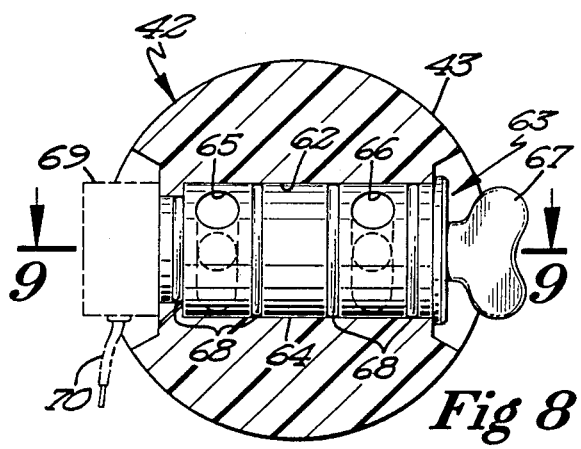
FIG. 8 is a cross-sectional view taken approximately along the line 8—8 of FIG. 2 and looking in the direction of the arrows.

The manifold unit 43 is also provided with a cylindrical recess 62 therethrough, which accommodates a rotatable valve 63. The rotatable valve 63 includes a generally cylindrical valve body 64 having a pair of spaced apart valve ports 65 and 66 therethrough, as best seen in FIGS. 8, 9, 14, and 15. The valve body 64 is provided with a small handle 67 at one end thereof to facilitate the rotation of the valve body in the manifold body. The valve body is also provided with axially spaced apart angular seals 68 of well-known construction, as best seen in FIG. 8. A photoelectric position sensor unit 69 is secured to the valve body 64 and is provided with suitable electrical conductors for sensing the position of the valve body during operation of the gas-sensing apparatus 10. In this regard, the valve body is rotatable through an arc of 90 degrees to selectively intercommunicate the passages 49 and 50 with the mass spectrometer or to intercommunicate the passages 51 and 52 with the mass spectrometer device. This arrangement permits lung gases to be sampled and measured or, alternatively, tracheal tissue gases to be sampled and measured. The photoelectric sensor unit 69 will produce a visual signal indicating which sampling procedure is being monitored.

Referring now to FIGS. 10, 11, 13, and 16, it will be seen that the manifold unit is connected to an air driven gear motor pump unit 71, which is comprised of a generally cylindrically shaped motor pump body 72. Any suitable means, such as locking pins or the like, may be used to detachably secure the gear motor pump unit 71 to the manifold unit 62. The motor pump body 72 has a hollow interior provided with a non-magnetic divider plate 73 that divides the interior of the pump body into a motor chamber 74 and a pump chamber 75. The divider plate 73 engages an annular shoulder 72a in the pump body 72 for properly positioning the divider plate. The divider plate 73 has spaced apart axle pins 76 and 77 projecting from one surface thereof. The axle pins 76 and 77 project to the motor chamber 74, and each defines the center of a pair of cylindrical sub-chambers of the motor chamber. The divider plate 73 also has spaced apart axle pins 78 and 79 extending from the other surface thereof and projecting into the pump chamber 75. It will also be noted that the axle pins 78, 79 each define the center of a pair of sub-chambers of the pump chamber. It will further be noted that the axle pin 76 is disposed in coaxial relation with the axle pin 78, while the axle pin 77 is disposed in coaxial relation with axle pin 79.

Referring again to FIGS. 9, 10, 11, and 14, it will be seen that the motor pump body 72 is provided with a pair of laterally spaced apart axially extending passages 80 and 81 therein. The motor pump body 72 is also provided with an axially extending passage 82 therein and a radially extending passage 83 therein. The passages 80 and 81 communicate with the pump chamber 75, while the passages 82 and 83 communicate with the motor chamber 74. The passage 80 defines a sample passage through which sample gases from either the lung or tracheal sampling cell are directed, while the passage 81 defines a return passage through which lung gas samples or tracheal tissue gas samples are returned. The passage 82 defines an air inlet passage, which provides the motive power for driving the motor pump unit. The air passage 83 defines an outlet passage through which the air under pressure for driving the motor pump unit is discharged. In this regard, the pump body is provided with a fitting 84 having a hose 85 connected thereto through which air is discharged from the air outlet passage 83.

Referring again to FIG. 10, it will be seen that an upper drive gear 86 has a central opening 87 therein and is journaled on the axle pin 76 for rotation relative thereto. Drive gear 86 is provided with a plurality of gear lobes 88 symmetrically arranged and disposed in meshing relation with a lower driven gear 89. The lower driven gear 89 is provided with a central opening 90 and is journaled on axle pin 77. The lower driven gear 89 is also provided with gear lobes 91, each having a magnetic element 92 embedded therein. The drive gears 86 and 89 are shaped to be positioned within the motor chamber 74 so that the outer peripheries of each gear lobe are disposed closely adjacent the inner surfaces of the motor chamber. Again, it will be noted that the axis rotation of the drive gear 86 and the driven gear 89 each define the center of the sub-chambers of the motor chamber 74.

Figure 11:
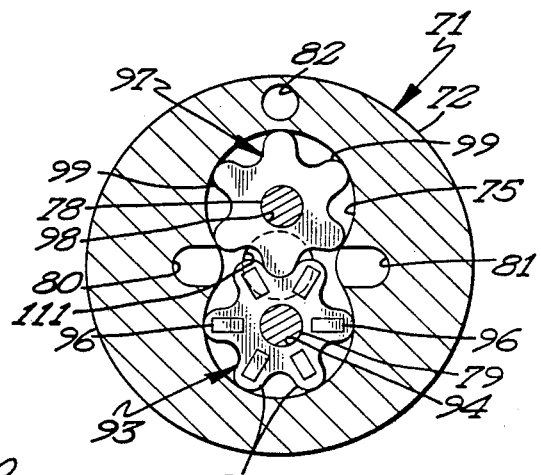
FIG. 11 is a cross-sectional view taken approximately along the line 11—11 of FIG. 2 and looking in the direction of the arrows.
Figure 9:
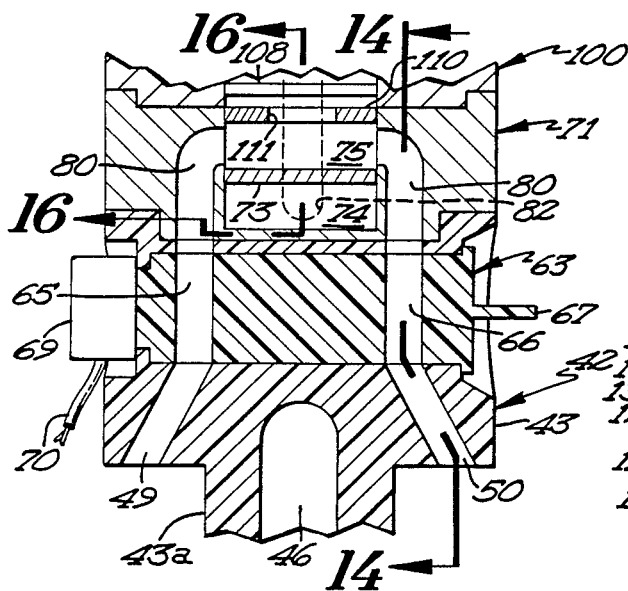
FIG. 9 is a diagrammatic cross-sectional view illustrating the location of certain passages in the valve in the manifold block.
Figure 12:
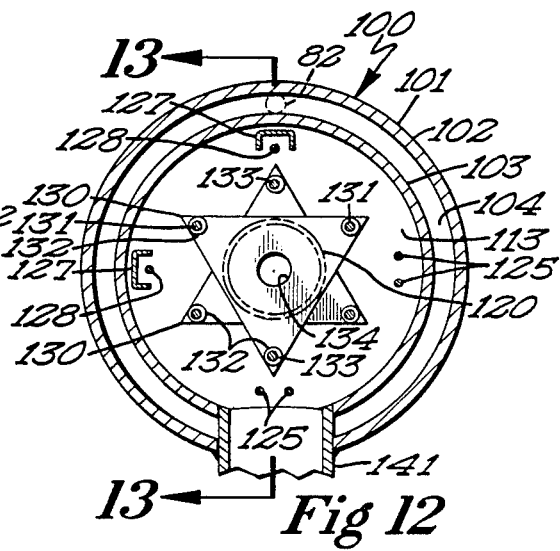
FIG. 12 is a cross-sectional view taken approximately along the line 12—12 of FIG. 2 and looking in the direction of the arrows.

Referring now to FIG. 11, it will be seen that the pump chamber 75 is provided with a lower driven gear 93 having a central opening 94 therein and is journaled on axle pin 79. The lower driven gear 93 has a plurality of symmetrically arranged gear lobes 95, each having one of a plurality of soft iron core elements 96 embedded therein.

The driven lower gear 93 in the pump chamber 75 is disposed in meshing relation with a driven upper gear 97 having a central opening 98 therein and journaled on axle pin 78. The driven gear 97 is also provided with gear lobes 99. It will be noted that the outer peripheral surfaces of the gear lobes of the driven gear 93 and the driven gear 97 are disposed closely adjacent the inner surfaces of the pump chamber 75. It will also be noted that, when the drive gear 86 of the air driven motor pump is driven by a stream of air under pressure introduced through the passage 82, gear 86 will drive the gear 89 and this rotating motive force will be transmitted by the interacting magnetic elements and soft iron core elements 92 and 96, respectively, to drive the lower gear 93 and, ultimately, the gear 97. The air stream for driving the motor unit is constantly being exhausted through the air passage 83 during operation of the motor unit and the pump unit.

The motor pump body 22 is provided with a closure plate 110 having a central outlet opening 111 therein. Gas samples from either the lungs or the tracheal tissue sample cell are exhausted from the pump chamber 20 through the outlet opening 111 into the mass spectrometer device 100.

Figure 13:
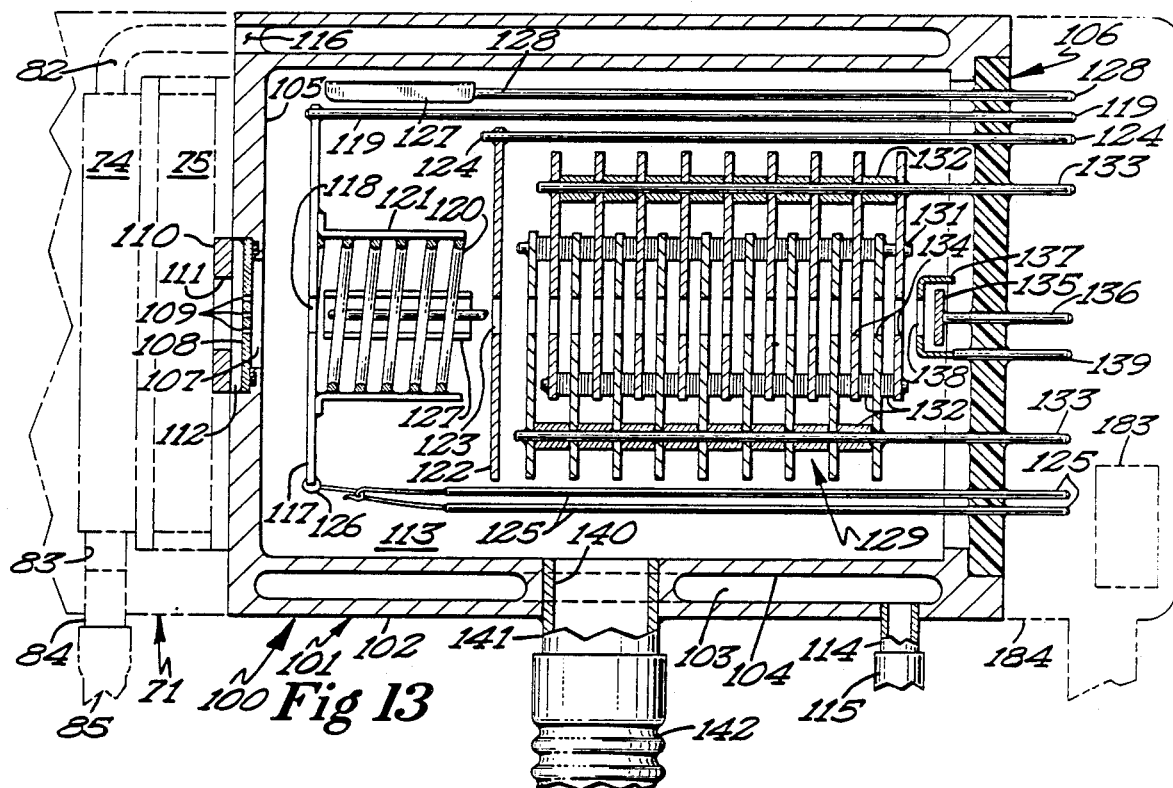
FIG. 13 is a cross-sectional view taken approximately along the line 13—13 of FIG. 12 and looking in the direction of the arrows.
Figure 14:
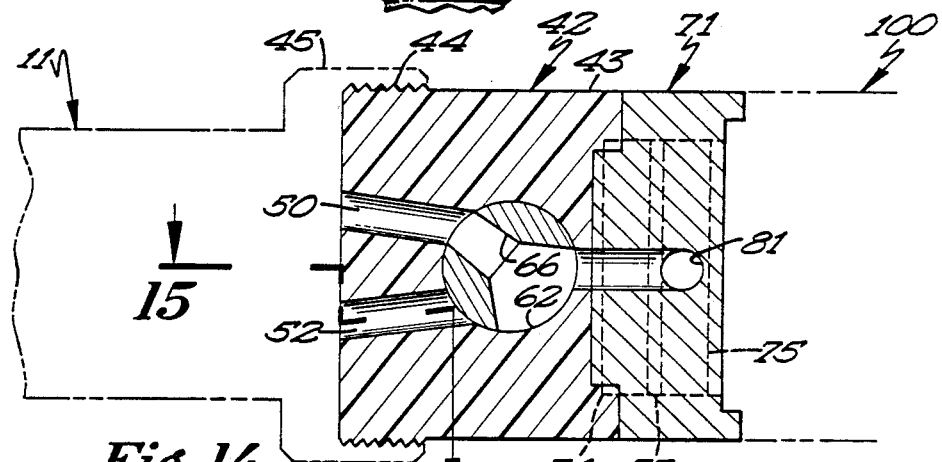
FIG. 14 is a cross-sectional view taken approximately along the line 14—14 of FIG. 9 and looking in the direction of the arrows, but rotated through an arc of 90 degrees.

Referring now to FIG. 13, it will be seen that the motor pump unit 71 is detachably connected to a miniature mass spectrometer device 100, which includes a housing or body 101 of generally cylindrical configuration formed of stainless steel or the like. Although not shown in the drawings, it is pointed out that the mass spectrometer housing 101 will be connected to the motor pump body 72 by any suitable releasable connecting means, such as coupling pins or the like, to permit easy and ready connection and disconnection of these units.

The mass spectrometer housing 101 is of double wall construction and includes an outer cylindrical wall 102 and an inner cylindrical wall 103 spaced from the outer wall to define a generally cylindrical cooling chamber 104 therebetween. The housing 101 also includes a front end wall 105 integral with the cylindrical inner and outer walls. A generally circular ceramic header 106 defines the rear wall of the housing 101 and engages the double cylndrical walls thereof in sealing relation therewith.

The front end wall 105 is provided with an axial opening 107 therein, which is closed by a closure plate 108, having laser formed inlet ports 109. In the embodiment shown, three inlet ports are provided through which the sample gases to be measured pass. The inlet ports 109 are closely grouped together and each is of approximately 2.5 microns diameter. The use of three separate ports to the mass spectrometer allows for redundancy with regard to blockage by foreign matter. Since the spectrometer vacuum system is operated in a conductance limited regime, obstruction of one or more ports will be immediately recognized by a change in the operating pressure. Such blockage will be flagged to the operator, but will not impede the continuing use of the spectrometer.

Sample gases to be measured are exhausted through the outlet passage 111 of the motor pump unit and into the inlet ports 109 of the mass spectrometer device. However, it will further be noted that a volumetric accumulator space 112 is defined between the closure plate 108 of the mass spectrometer device and the closure plate 110 for the pump chamber 75.

The sample gases to be measured are directed through the inlet ports 109 into the interior 113 of the mass spectrometer housing 101. It will be noted that the housing 101 is provided with an inlet passage fitting 114 which communicates with the cooling chamber 104. The inlet fitting 114 is provided with a hose 115, which is connected to a source of cooling air under pressure for controlling the temperature of the interior 113 of the mass spectrometer device. It will further be noted that a passage 116 intercommunicates the cooling chamber 114 with the air inlet passage 82 in the motor pump body 72. Thus, it will be seen that air under pressure, which is used to cool the mass spectrometer, is also used to drive the motor pump gear drive unit 71.

Referring again to FIG. 13, it will be seen that a circular entrance plate or electrode 117, having a central opening 118 therein, is spaced from, but positioned adjacent the closure plate 108 with the opening 118 generally in alignment with the inlet ports 109. The entrance plate 117 is connected to a suitable electrical conductor 119 which extends through and is fused in the header 106. A grid helix or cage 120 is welded or otherwise secured to the entrance plate 117 and projects therefrom. A pair of small wire brackets 121 is secured to the entrance plate 117 and to the coils of the grid helix 120.

It will be noted that the axis of the grid helix 120 is disposed in coaxial relation with the opening 118 in the entrance plate. A circular end plate or extractor electrode 122, having a central opening 123, is connected to an electrical conductor 124, which projects through and is fused to the ceramic header 106. The opening 123 in the end plate 122 is disposed in coaxial relation with the opening 118 and the axis of the grid helix 120. The volumetric space defined within the grid helix 120 defines an ionization zone and with the entrance and end plates constitutes components of an ion generator.

The ion generator also includes a pair of electron emission filaments, which are disposed at an angle of 90 degrees relative to each other, and the filaments are made of palladium and coated with conventional barium-strontium emission compound. In normal operation, one of these filaments is heated until it is emitting electrons, while the other filament is maintained in a warm condition in order to maintain it free of contaminants. Should the filament in use break, or otherwise fail, then the second filament will be heated to take over the supply of electrons. The energized filament is maintained at a potential of 100 volts negative to the wire grid helix 120 and electrons are, therefore, accelerated to an energy of 100 e.v. in the gap between the energized filament 125 and the grid helix 120.

On arrival at the grid helix 120, some of the electrons land on the wire, causing a flow of current, which is normally called the emission current. This current is sensed by the electronic circuitry, in a manner to be more fully described hereinbelow, and is stabilized to a constant value by altering the power supply to the filament.

Other electrons pass between the turns of the grid helix and into the ionization zone. It is pointed out that the ratio of electrons hitting the grid, and thus providing the stabilization information, to electrons passing into the ionization zone is determined solely by the transparency of the grid. The transparency of the grid is the ratio of wire diameter to the turn spacing.

Inside the grid, some of the electrons collide with the gas molecules, thereby producing ionization and fragmentation, while other electrons pass through the grid without interacting with the molecules or without striking the grid coils. These non-interacting electrons pass into a generally U-shaped trap electrode 127, which is maintained at the same potential as the grid helix 120. In this regard, each filament 125 has a U-shaped trap electrode 127 disposed in diametrically opposed relation therewith. Each U-shaped trap electrode is provided with a single central ion collector wire 128 which monitors the total number of ions generated per unit time and, hence, measures the gas pressure inside the spectrometer. The ion collector wire 128 for each U-shaped trap electrode 127 projects through and is fused in the header 106.

The number of ions generated within the grid helix, therefore, depends on the number of ions of a given species within the grid helix, the ionization cross-section of a given species, when bombarded with 100 e.v. electrons, and the density of electrons within the grid helix. As the electron density is maintained constant by the emission stabilizer and the ionization cross-section does not vary with time, the number of ions of a given species generated per unit time depends only on the partial pressure of that species within the ionization zone. The ions migrate to the end of the grid helix 120 remote from the entrance aperture 118 in the entrance plate 117. A fraction of these ions passes through the opening 123 in the end plate 122 and into the linear accelerator mechanism 129 of the spectrometer.

It will be appreciated that the components of the spectrometer, within the interior 113 thereof, including the linear accelerator mechanism, are all built or attached to the multi-pinned glass or ceramic feedthrough header 106, which is of general standard construction. The linear accelerator mechanism 129 is comprised of a plurality of substantially identical axially spaced apart triangular plates or acceleration electrodes 130, which are stacked or mounted on mounting rods 131 provided with annular separator or spacer elements 132 formed of mica. An elongate upper bus rail 133 and a lower bus rail 133a provides energy for the plates 130, and these bus rails project through and are fused to the header 106. In the embodiment shown, the plates 130 are connected alternately to each rail 133 and rail 133a. For example, plates 1, 3, 5, 7, and 9 . . . are connected to the uppermost rail 133 illustrated in FIG. 13, while plates 2, 4, 6, 8 . . . are connected to the lowermost rail 133a. The plates 130 each have a central opening 134 therein, and these openings are disposed in axial alignment with each other and with the opening 123 of the extraction electrode 122.

The linear accelerator is also provided with an ion collector element or plate 135 positioned closely adjacent the header 106 and in alignment with the axes of the openings 134 of the accelerator electrodes 130. The ion collector plate 135 is provided with a suitable electrical conductor 136, which projects through and is fused to the header 106. A shield box 137 is positioned around the ion collector element 135, but is provided with an aperture 138 therein, which is also disposed in axial alignment with the openings 134 of the accelerator electrodes. The shield box 137, which is secured to an electrical conductor 139 mounted in the header 106, serves to minimize the radio frequency transferred to the low level ion collector plate 135.

It will be noted that the mass spectrometer housing 101 has an opening 140 therein, which communicates with the interior 113 thereof. A fitting 141 is secured to the housing in the opening 140 and is provided with thin-walled steel hydroformed bellows 142 having an effective diameter of 1.5 centimeters and connected to a vacuum source, such as the vacuum pump VP, as best seen in FIG. 17. It is pointed out that since the mass spectrometer device is of miniature construction and, in the embodiment shown, has a path length of the order of one centimeter, the spectrometer may be operated at a vacuum of $1E^{-3}$ torr. Vacua of this magnitude may be obtained by remote pumping, and it is these parameters which permit the motor pump and mass spectrometer module to be mounted directly on the end of the endotracheal tube. Although the spectrometer shown has a path length of approximately one centimeter, it is pointed out that miniature spectrometers having a path length within the range of approximately one-half to two centimeters would also be effective.

In order to understand the operation of the mass spectrometer, the potentials existing therein must be defined. As pointed out, the electron emission filament 125 is operated at a constant 100 volt potential negative to the grid helix 120 and the entrance plate 117. The grid helix 120 and the entrance plate 117 are operated a few volts negative to ground potentials and ions formed within the grid helix or cage 120 exist with epithermal energies at a potential a few volts below ground potential. The exact potential of the initial ions can be adjusted during initial setup of the spectrometer in order to set the spectrometer mass resolution to the desired value.

The ion collector wire 128 of each U-shaped trap electrode 127 is operated at a potential 20 volts negative to the associated electron emission filament 125, thereby attracting positive ions, while preventing electrons from the filament from landing on the collector wire. It is pointed out that each U-shaped trap electrode and its associated ion collector wire is substantially identical to that of the conventional Bayard Alpert ionization gauge. In normal Bayard Alpert gauge practice, the ion collector wire is operated at zero potential in order to minimize leakage current to and from the collector wire to ground or other electrodes. However, in the present embodiment, the ion current is relatively large due to the high operating pressure of the spectrometer and so there is negligible loss of sensitivity or stability associated with this method of operation.

The end plate 122 of the ionization zone is operated at a potential of 5 volts more negative than the grid helix 120 and the entrance plate 117. Ions in this zone are, therefore, attracted to the end plate 122 and pass through the opening 123 therein into the linear accelerator mechanism 129.

As soon as the ions pass through the end plate 122 of the ion generator, they are accelerated by a potential of $-100$ volts supplied to the first electrode 130 of the linear accelerator 129. This acceleration achieves two desirable effects, namely, it reduces the velocity spread of the ionized particles to the order of 2.5%, and the end plate 122 and the first accelerator electrode 130 of the linear accelerator electrically cooperate with each other to form a gap lens. The particles coming from the ionization zone are diverging, and this gap lens reconverges the particles so they will focus at the upstream end of the linear accelerator 129. As the linear accelerator 129 is itself focusing, the strength of this first lens is adjusted (by adjusting the spacing between the end plate 122 and the accelerator electrode 130) so that the ions of interest are focused on the ion collector plate 135 at the downstream end of the linear accelerator 129.

The accelerator plates 130 are energized by the bus rails 133 and 133a, and these bus rails are both maintained at the same potential as the initial accelerator electrode downstream of the end plate 122. However, each of the bus rails 133 and 133a have a superimposed symmetrical radio frequency voltage whose peak value is 5 volts. Therefore, at a given instant of time, if the uppermost rail 133 is at +3 volts relative to the acceleration voltage, then the lowermost rail 133a is at −3 volts. Consider now an ion in the linear accelerator 129 is when plate 1 is at +5 volts, and plate 2 is at −5 volts. This ion will be accelerated by a 10-volt potential and will enter plate 2 with an energy 10 electron volts greater than before.

Suppose the velocity of this ion is such that, during its passage through the thickness of plate 2, the time taken was equal to one-half cycle of the radio frequency energy. When the ion emerges from the plate 2 and crosses the gap into plate 3, the lowermost bus rail 133a and plate 2 is now at a potential of +5 volts, while the uppermost rail 133 and plate 3 is at a potential of −5 volts. This ion, therefore, gains a further 10 electron volts of energy on entering the third plate. If the thickness of the plates or electrodes is chosen so that this ion stays in phase, always taking a time equal to a half cycle of the radio frequency to traverse the plate, then it will receive a 10 electron volt energy gain at each gap, finally emerging from a 5-gap, 6-plate stack, with 150 electron volts of energy.

Consider now a continuous flux of ions, all with the correct initial velocity to traverse the thickness of a plate in one-half cycle of the radio frequency, but arriving at all possible times with respect to the potentials of the radio frequency cycle. Some of the ions will arrive in gaps, as described above, at the optimum time; some will arrive when there is no radio frequency potential difference, and will pass through the structure without acceleration, while still others will arrive when the radio frequency potential is in the retarding direction and, thus, will exit at the stack with less than the initial 100 e.v. of energy.

Now consider an ion which arrives at the accelerator stack with the correct velocity. No matter what its arrival time in the first gap with respect to the instantaneous potentials due to the radio frequency energy, due to the different time this ion will take to traverse the thickness of the plates, its instant of traversing the inner plate gaps can never exactly coincide with the maximum accelerating potential difference at each gap. The phase of this ion is constantly changing relative to the phase of the radio frequency potential difference across each gap. At best, such an incorrect velocity ion will receive only a part of the maximum acceleration and will exit the gap structure with less than the maximum possible energy.

The velocity, therefore, is proportional to the inverse square root of the mass. Therefore, for a given frequency of the radio frequency energy, there will only be one mass of ion which has the correct velocity to receive maximum acceleration when crossing all of the gaps. Altering the frequency of the radio frequency energy will, therefore, alter the optimum dwell time in each plate. Changing the radio frequency is, therefore, the method of tuning the spectrometer to optimally accelerate ions of different velocities and, therefore, different masses.

In order to perform the desired measuring function, one must identify the ions, which have been optimally accelerated by all gaps of the accelerating section. The ions are collected by the ground potential electrode plate 135 facing the opening 134 in the last accelerator plate 130. Since the ions were generated in the ionization zone at a potential negative relative to zero, unaccelerated ions cannot land on the collector plate 135. By changing this potential to more negative values, one can require more and more acceleration to have been obtained by an ion before it can land on the collector plate surface and, thus, produce an ion current signal as a measure of the ion flux. For example, if the grid helix 120 is operated at a potential of −30 volts, then ions need to gain 30 electron volts (e.v.) in the linear accelerator in order to land on the collector plate. Thus, by requiring an energy gain of a predetermined magnitude, only ions, for example, of one mass can land on the collector plate 135. This selectivity can be varied at will by altering the required energy gain, naturally at the expense of rejecting more of the ions of the correct mass.

In order to examine the quantitative form of the ion flux curves, an effective method is to perform a monte carlo calculation, starting with particles with different velocities, and different projection angles at the entrance to the linear accelerator 129 at random times relative to the radio frequency cycle. Following these particles through the accelerator stack then enables a flux distribution for any combination of particle velocity (and, therefore, mass) and radio frequency to be obtained.

While the mass spectrometer device 100 has the inefficiency that many of the ions of the selected mass do not land on the ion collector plate 135 because these ions arrive at the first gap of the linear accelerator 129 at the wrong phase of the radio frequency cycle, this inefficiency is of no moment in the present application. It will be appreciated that, since the acceleration of the ions is produced by an axial electrical field, differentiation between ion species can be obtained in an extremely compact structure. As pointed out above, the mean free path needed for the majority of the ions to be able to reach the collector plate 135 without large angle collisions is very small, which implies that the mass spectrometer device 100, of the embodiment disclosed will work effectively at pressures around $10E^{-3}$ and up to $10E^{-2}$ torr. Further, since the present mass spectrometer device measures respiratory gases from human subject, these sample gases are available in liter quantities at atmospheric pressure on the atmospheric side of the inlet ports or orifices 109 of the mass spectrometer.

Referring now to FIGS. 5 and 6, it will be seen that a disposable mouthpiece device 143 is there shown and constitutes an alternate form for the endotracheal tube as a device for continuously circulating the gases to be measured through the motor pump and mass spectrometer module 12. The disposable mouthpiece device 143 is formed of a suitable flexible plastic material and includes a double-walled mouthpiece tube 144 comprised of an inner tube 145 and an outer tube 146. Although not shown in the drawings, suitable interconnecting wall elements interconnect the inner and outer tubes and define four auxiliary passages, rather than the seven passages embodied in the endotracheal tube 11. The inner tube 145 defines a large central passage in the manner of the endotracheal tube. Referring again to FIG. 6, it will be seen that the mouthpiece tube 144 is provided with an elongate passage 148 and an elongate passage 149, which extends throughout the length of the mouthpiece tube. The lower end of the mouthpiece tube is provided with an opening 150, which communicates with passage 148, and an opening 151, which communicates with passage 149. The sample gases from the lungs will directed through the opening 50 and upwardly through the passage 148, while a portion of these gases will be returned through the passage 149 and discharged through the opening 151. Thus, the passage 148 constitutes a sample gas passage, while passage 149 defines a return passage.

A face engaging flange element 152 is secured to the outer tube 146 and is adapted to engage the exterior surface of the face of the human subject adjacent the subject's lips. A capillary restriction member 154 is positioned adjacent the lower end portion of this mouthpiece tube, and the capillary restriction member is provided with a plurality of capillaries or passages 155 which extend therethrough, as best seen in FIG. 6. In this regard, the construction of the capillary restriction member is substantially identical to that shown in the endotracheal tube.

The inner tube 145 is provided with an opening 157 therein located below the capillary restriction member 154 and is also provided with an opening 158 therein adjacent, but spaced above the capillary restriction member. Although not shown in the drawings, opening 157 communicates with a passage that directs lung gases via the manifold unit to the differential pressure transducer. Similarly, opening 158 also communicates with a passage that directs the lung gases through the manifold unit to the differential pressure transducer. The disposable mouthpiece device 143, therefore, permits measurement of the lung gases by the mass spectrometer and also permits measurement of the lung capacity by means of the differential pressure transducer.

The disposable mouthpiece device is intended primarily for conscious non-anesthetized patients for use in assessing cardiac output and other cardio-respiratory functions during office visits, exercise testing, such as a treadmill procedure or measuring response to drugs. It will be appreciated that the mouthpiece device will not have the degree of efficiency of the endotracheal tube, since the lung gases are being obtained at the rear portion of the human subject's mouth. The dead space defined between the rear or lower end portion of the mouthpiece device and the lower tracheal or bronchial tree area naturally renders the mouthpiece device less efficient than the endotracheal tube. However, the mouthpiece device can be readily used with conscious patients with little or no discomfort.

Referring now to FIGS. 17 and 18, it will be seen that the spectrometer electronics in cooperation with the mass spectrometer 129 are there shown in diagrammatic form. The electronic circuitry is designated generally by the reference numeral 160 and is comprised of a base unit 161 and a head unit 162. The head unit is of light portable construction, containing the computation readout and operator input and may be mounted on the anesthesist's trolley, as illustrated in FIG. 17. The base unit does not require the operator or anesthesist to manipulate or otherwise interact with the components thereof and therefore may be positioned at floor level with other components, such as the vacuum module.

Since the spectrometer requires potentials of approximately 100 volts, and is in close proximity to the patient, all the spectrometer electrical supply requirements are constructed as a ground isolated system, using isolating transformers and construction approved for this application. The purpose of such a ground isolated system is to insure that a leakage to ground via the patient, or otherwise, causes an unmeasurable flow of current, thus, protecting the patient from harm. In addition, active ground current monitoring from the isolated electronics will produce an immediate shut-down and notify the operator of fault conditions.

Transmission between the head and base unit is by two fiber optic lines which not only provide ground isolation, but also eliminate the transmission of electromagnetic interference to the head unit. In the embodiment shown, one of the fiber optic lines 165 transmits information to change the frequency of the radio frequency energy applied to the spectrometer in order to tune ions of different mass. The outgoing fibre optic line 166 provides digitized information of the ion current at the spectrometer collector plate 135, the ion current collected by the ion collector wire 128, as well as monitoring the potential supplied to the spectrometer system in absence of fault conditions.

The base unit 161 includes a D.C. power source 163 which is provided with a filament electrical current supply 164, which is controlled by the electron emission current received on the grid helix 120 of the ionization zone, and which stabilizes this emission current at a given value. The filament current supply 164 also senses for a voltage applied—no filament current flow situation, and if found switches over to the second filament. The head unit is notified of the switchover and flags the operator by a visual or audible signal. During start-up of the apparatus 10, the head unit also senses and determines that current is flowing through both filaments and start-up is prevented if only one filament is operable. The current to the inactive filament will be supplied through a resistor until the additional filament is needed.

The D.C. power unit 163 is also provided with a 100-volt electron acceleration current supply 168, which forms the feedback signal for the filament supply 167. A 120-volt supply current 169 serves to bias the pressure sensing ion collector wire 128. This current is isolated from the rest of the spectrometer and supplies zero volt bus so that the ion current flow can be sensed at bus potential and transmitted to the head unit 162.

A 100-volt current supply 170 supplies the current to operate the linear accelerator 129. This current supply is modulated at audio frequency by a sinusoid of 1–2 volts amplitude. The final ion current in the ion collector plate 135 is phase detected with the audio signal as a reference. The resultant output is used to vary the exact value of the 100-volt potential in order to maximize the ion current, that is, to have a minimum first harmonic component in the phase detected ion signal. This correction maintains the spectrometer 100 in tune, as well as compensating for dimensional tolerances in the spectrometer head and possible slump of the structure due to mistreatment. This seeking function is responsible for the maintenance of the spectrometer 100 in calibration without day-to-day adjustment by an operator.

A programmable D.C. supply unit 171 has a 30-volt programmable current supply or conductor 172, which is controlled by input from the head unit 162. The current supply 172 sets the potential at which the ions are generated and, therefore, the acceleration that they must obtain in order to land on the grounded ion collector plate 135. The potential of this supply is also sensed by the head unit 162.

The base unit 161 also includes a programmable radio frequency generator 173 whose radio frequency signal is transmitted to the spectrometer by two coaxial cables 174, each terminated by its iterative impedance. The radio frequency generator consists of a group of quartz crystal controlled oscillators, together with harmonic multipliers, and a wide band power amplifier capable of delivering a 5-volt peak amplitude radio frequency signal to the spectrometer. The output level is rectified and fed back to the power amplifier in order to keep the amplitude of the radio frequency amplitude constant. Switching between oscillators is performed on command by control means of the head unit 162 in order to select different ion species for analysis. In general, the switching rate between ion species will be determined by the settling time of the ion collection amplifier.

The base unit 161 is also provided with an auxiliary thermistor and pressure transducer power unit 175 having a current supply conductor 176 and a current supply conductor 177 electrically connected with a pair of auxiliary thermistors, the function of which will be set forth more clearly hereinbelow. A pair of current supply conductors 178 also electrically connects the power unit 175 with a differential pressure transducer 179. Output signals from the differential pressure transducer 179 are transmitted to a multiplexor unit 180 via conductors 181. The multiplexor unit 180 is a component of a data acquisition system, which also includes a 10-bit analogical digital converter 182 and control electronics for transmitting the digitized information to the head unit 162.

The multiplexer unit 180, as well as transmitting spectrometer ion current data, spectrometer pressure ion current data, and parameters of the spectrometer, also transmits data obtained from zener reference sources in order to check the continual functionality of the multiplexer-analog digital converter system.

An ion current amplifier 183 is mounted as a head amplifier in the connection socket 184 of the mass spectrometer header 106 and is followed by a second amplifier (not shown) at the module end of the connecting cable for the connection socket. The use of a head amplifier eliminates the problems associated with a large cable capacitance which would otherwise be associated with a remote amplifier.

The head unit 162 constitutes a system controller, which communicates with the spectrometer system through the fibre optic cables 165 and 166, as described hereinabove. The system controller actually constitutes a micro-computer 185 to serial input-output ports and can be fabricated from any of the commercial central processing units of desired capacity. In the embodiment shown, it will be seen that the micro-computer or CPU has been duplicated for maximum reliability and for continuation of monitoring, should a run wild or halt occur in the system. It is also pointed out that each CPU is provided with a watch dog set to detect malfunction.

The system also includes a display and user interface 186, which may be a conventional screen-keyboard, a custom LCD panel, or a touch-sensitive input tablet. The head unit includes a digital analog converter 187, which can be operated from the incoming signal line from the head unit 162. The digital analog converter 187 is connected through one of the multiplexor unit channels to the analog digital converter 182. Startup testing, therefore, programs a staircase wave form on the digital analog computer, with the analog digital converter 882 converting each step. This enables the monotonacity in the absence of missing codes to be checked by both the digital analog converter 187 and the analog digital converter 182. Under operating conditions, the digital analog converter 187 sets the levels of the power supply, which generates the starting potential of the ions.

Although not shown in the drawings, provision is made for an output line to a central recording area where the spectrometer data can be continuously recorded in a tamper resistant environment in order to provide information on the progress of the patient during surgery, and to have documentation available for future use, such as possible future litigation.

During operation of the apparatus, the rotatable valve 63 in the manifold unit will be manipulated to a position for measuring the sample gases from the lower trachea or from the tracheal sampling cell 39. If the lung gases are being sampled, then the head unit of the apparatus will indicate that this function is being performed and that the tracheal sampling cell 39 is not in use.

In a normal man, during the steady state, lung profusion and cardiac output are essentially equal. All $CO_2$ recovered and all $O_2$ consumed from the respiratory air reflects right ventricular blood flow. Since the output of the right and left ventricles are virtually identical, this is the cardiac output. The general equation expressing this relationship is the well-known form of the Fick equation:

$$Q = Vx/(Cax - Cvx)$$

where
 $Q$ = cardiac output
 $Ca$ = arterial concentration of x
 $CVx$ = mixed venous concentration of x
 $Vx$ = total amount of x.

This expression is positive for uptake conditions ($X = O_2$) and negative for output conditions ($X = CO_2$).

The cardiac output may be measured by a single breath procedure or by a $CO_2$ rebreathing method. The single breath method uses the respiratory exchange ratio taken during a prolonged expiration (10 seconds). A detailed discussion of the single breath method and the computations used therein are expressed in the article entitled, "Estimation of True Venous and Arterial $PCO_2$ by Gas Analysis of a Single Breath", by T. S. Kim, et al., appearing in the *Journal of Applied Physiology*, 21(4): 1338–1344; 1966.

The respiratory exchange ratio taken during a prolonged expiration (10 seconds) is expressed as follows:

$$(R) = \frac{V\ CO_2}{V\ O_2} = \frac{CV\ CO_2 - CACO_2}{C_a\ O_2 - CVO_2}.$$

In the operation of the subject apparatus, the mass spectrometer R produces data which is continuously calculated during a prolonged expiration, giving rise to a curve. The slope (S) of the tangents at various intervals is used to derive a family of instantaneous R values from the following form of the alveolar air equation:

$$S = \frac{R = (I - R)\ FACA_2}{I - (I - R)\ FAO_2}$$

Solving for R:

$$R = \frac{S - (FAO_2 \times S) - FACO_2}{I - (FAO_2 \times S) - FAO_2}.$$

The various instantaneous values of R are then plotted against their corresponding measured $PCO_2$ (arterial-alveolar). This allows the estimation of the appropriate arterial and mixed venous $CO_2$ tensions that must have existed. The arterial $PCO_2$ is obtained from the R value averaged from several normal expired breaths preceding a greater than normal inspiration followed by a prolonged expiration (10 seconds).

In man, the time mixed venous $PCO_2$ is obtained from the R value intercept at R=0.32. At this value of R=0.32, arterial and venous $PCO_2$ are equal (no pressure gradient), yet $CO_2$ is still exchanging at one-third the usual rate because of the Haldane effect. At R=0.32 every unit volume of $O_2$ taken up by hemoglobin from the venous blood displaces exactly 0.32 volumes of $CO_2$ without a change in $PCO_2$. Thus, by determining precisely the alveolar-arterial $PCO_2$ when the instantaneous exchange ratio (R) has fallen to 0.32, a value is obtained which must be equal to the mixed venous $PCO_2$.

The key to this single breath method is the ability to determine $PO_2$ and $PCO_2$ at the same instant in time which is made possible by the miniature mass spectrometer attached to the upper end of the endotracheal tube or mouthpiece device, thereby eliminating a maximum amount of dead space. The correlation of ths data with heart rate is critical in the single breath method.

When the cardiac output is determined by the $CO_2$ rebreathing method, this method is also simple and is carried out in less than 30 seconds. Specifically, this method depends on assessing the time it takes for rebreathed $CO_2$ to reach a plateau. The precise detail of this method is described in an article entitled, "Cardiac Output Determination by Simple One-Step Rebreathing Technique", by L. E. Farhi et al., published in *Respiration Physiology* (1976), 28, 141-159. However, the present apparatus obviously increases the accuracy and shortens the time needed to reach a plateau because the dead space is reduced.

Heart beat correlation with the $CO_2$ rebreathing method is important, but not as critical as with the single breath method. It is pointed out that, during the single breath method and the $CO_2$ rebreathing method, the lung gases are circulated through the sample gas passage 20 in the endotracheal tube and are returned through the return passage 19. If the mouthpiece device 143 is used, the sample gases are directed upwardly through the sample gas passage 148 and are returned through the return passage 149.

The lung capacity or volume is determined by the differential pressure transducer and received gas samples from below and above the capillary restriction member 27 in the endotracheal tube or the capillary restriction member 154 in the disposable mouthpiece device. The location of the restriction capillary member 27 in the endotracheal tube or the capillary restriction member 154 in the mouthpiece device is chosen so that the temperature of the capillaries will be close to body temperature, thus eliminating condensation of moisture within the capillaries. Flow of gases through these capillaries produces a pressure differential which is communicated through their associated passages to the differential pressure transducer for measuring respiratory volume.

Although both of the balloons 33 are inflated and serve as retention members during sampling of lung gases by means of the endotracheal tube, these balloons also define the tracheal sampling cell for use in making an analysis of the tissue cell gases. Sampling from this tracheal sampling spaced is undertaken when it equilibrates with the tracheal tissue and will measure tracheal tissue $O_2$ (and $CO_2$), which will closely reflect arterial $PO_2$. This sample gas will be representative of tissue $PO_2$ in other parts of the body and, therefore, indicate the accuracy of oxygenation This particular procedure should reduce or entirely eliminate the need for arterial samples, thereby making effective arterial $PO_2$ determination a non-invasive procedure of choice. Sampling from the tracheal sampling cells 39 is done by flushing argon gas through the openings or ports which communicate with the tracheal sampling cell and circulating the argon gas through the mass spectrometer for analysis until the argon gas reaches an equilibrium condition in the tracheal sampling cell.

It is also pointed out that, by introducing a tracer amount of gas, such as acetylene, into the expired mixture, the lung to trachea circulation time can be measured. This is a useful physiological measurement to assess the efficiency of blood circulation. Moreover, the uptake kinetics of acetylene can be used to assess local blood flow in tracheal tissues.

In addition to measuring the physiological parameters and characteristics set forth hereinabove, the present apparatus can measure other aspects of respiratory functions. In this regard, the apparatus can measure the anatomic respiratory dead space, the physiological respiratory dead space, the pulmonary diffusing capacity for $O_2$ and $CO_2$, and the anatomic and physiological shunt flow.

It will be appreciated that, regardless of the source of the gas samples being measured, these gas samples will be directed into the mass spectrometer via the motor pump unit 71. The use of an air driven gear pump insures that a steady flow of gases passes through the sampling orifices of the mass spectrometer. Even though a ripple in the flow rate occurs as a result of the meshing frequency of the gear teeth, this ripple in the flow rate is unimportant relative to the frequency of breathing.

In order to monitor the air flow, two thermistors are placed in the sampling gas stream. One of the thermistors is placed upstream of the circulator gears of the pump, and one is placed downstream of the circulator gears of the pump. The upstream thermistor will be used to correct the respired air volumes to standard temperature, while the downstream thermistor is supplied with sufficient electrical energy to self-heat it to a few degrees above the ambient temperature. Periodically, the flow of electrical energy to this downstream thermistor is interrupted and its cooling rate measured. The cooling rate will indicate that there is a continuous flow of gases around the measuring loop. If the sample gas passage or the return passage is blocked, or if, for any reason, the circulator gears do not rotate, the abnormal cooling rate of the downstream thermistor will make the instrument operator aware of this malfunction. The positioning of thermistors on opposite sides of the pump gears provides thermal isolation between them.

It will be appreciated that a major portion of the sample gases that are directed to the motor pump unit will be returned via the particular return passage and that only a small portion of the sample gas will be discharged into the mass spectrometer. The return of the sample gas the measured lung ventilation. This return and remixing of the sample gas reduces the delay time for the gas to reach the mass spectrometer analysis to a value negligible compared with inhalation and exhalation times.

From the foregoing, it will be seen that the novel gas sampling apparatus provides a non-invasive means for accurately and routinely monitoring cardiac output and the cardio-respiratory function in conscious, as well as anesthetized or unconscious, human subjects. Since the endotracheal tube and mouthpiece are disposable, the motor pump and mass spectrometer module may be readily disconnected therefrom and reused after centrifuging. The gas sampling efficiency of the apparatus, especially the endotracheal tube, is greatly enhanced by the elimination of dead space. The provision of a miniature motor pump - mass spectrometer module allows this efficiency to be obtained. Miniature mass spectrometers having a free mean path of the order of one-half to two centimeters in length are simply unknown in medical and related fields.

Thus, it will be seen that we have provided a non-invasive apparatus for assessing the cardiac output and other respiratory functions which functions in a more efficient manner than any heretofore known comparable apparatus.

What is claimed is:

1. An apparatus for sampling and analyzing the lung gases from a human subject, comprising:
    a gas sampling device for insertion into the mouth of a human subject including a double wall tube having upper and lower ends and including inner and outer tube elements, the interior of said inner tube defining a central passage therethrough, means dividing the space between the inner and outer tube elements into a plurality of elongate passages extending throughout the length of the double wall tube, a plurality of openings in the lower end portion of said inner tube element, each opening communicating with one of said passages, a capillary restriction member positioned within said inner tube having a plurality of capillary openings therein for restricting the flow of air through said central passage,
    a miniature motor pump mass spectrometer module, including a mass spectrometer, means connecting the mass spectrometer to a vacuum source, means connecting the motor pump mass spectrometer module with the upper end of said gas sampling device for intercommunicating a pair of said passages with said motor pump mass spectrometer module whereby lung gases are directed to said mass spectrometer,
    a differential pressure transducer with a pair of said passages whereby the gas pressure located below and above said capillary restriction member are sensed, and
    electronic circuitry cooperating with said mass spectrometer and said pressure transducer for analyzing the lung gases and lung capacity of the human subject.

2. The apparatus as defined in claim 1 wherein said gas sampling device comprises an elongate endotracheal tube which extends downwardly into the lower trachea of the human subject.

3. The apparatus as defined in claim 1 wherein said gas sampling device comprises a mouthpiece having a lower end terminating in the oral cavity of the human subject.

4. The apparatus as defined in claim 2 and means dividing the space between the inner and outer tubular elements into an elongate inflation passage, a tracheal sampling passage, and a tracheal return passage,
    a tracheal sample opening and a tracheal return opening in said inner tube communicating with said tracheal sample passage and a tracheal return passage, a pair of inflation openings in said outer tube, and
    a pair of inflatable balloon members secured to said outer tube element, each of said inflation openings communicating with one of said balloon members to permit inflation and deflation of the latter, said balloon members, when inflated, engaging the inner surface of the trachea of the human subject and cooperating therewith to define an annular tracheal sampling cell, said tracheal sampling opening and said tracheal return opening communicating with the tracheal sampling cell, means for selectively connecting said tracheal sampling and return passages to said mass spectrometer to permit tracheal tissue gases to be analyzed.

5. The apparatus as defined in claim 1 wherein said motor pump mass spectrometer module includes a motor pump unit including a motor pump housing having an outlet communicating with said mass spectrometer, a non-magnetic divider wall dividing the interior of said motor pump housing into a motor chamber and a pump chamber, a pair of revolvable meshing gears in said motor chamber, and a pair of revolvable meshing gears in said pump chamber, each gear in one chamber being coaxially disposed with a gear in the other chamber,
    co-acting magnetic elements on the gear in the motor chamber and on the co-axially disposed gear in the pump chamber,
    said pair of passages of said gas sampling device being connected in communicating relation with said pump chamber, and
    means connecting the motor chamber to a source of air under pressure to drive said motor chamber gears and thereby drive the pump chamber gears for directing sample gas into said mass spectrometer.

6. A disposable gas sampling device for use in obtaining respiratory gases for analysis from the human subject, comprising:
    an elongate flexible double wall tube for insertion into the mouth of a human subject, said double wall tube defining a central passage therethrough and having upper and lower ends and including inner and outer tubular elements,
    a plurality of axially extending, peripherally arranged auxiliary passages located between the inner and outer tubular elements of the double wall tube, including a gas sample passage, a return passage, and a pair of pressure sensing passages, a plurality of openings in the lower end portion of the inner tubular element, including a gas sample opening, a return opening, and a pair of pressure sensing openings, said gas sample opening communicating with said gas sample passage to permit lung gases to pass in an upward direction, said return opening communicating with said return passage through which lung gases are returned, each of said pressure sensing openings communicating with one of said pressure sensing passages, a capillary restriction member positioned within the inner tube element adjacent the lower end portion thereof and having a plurality of axially extending capillary passages therein for restricting the flow of gases through the central passage of the double wall tube, one of said pressure sensing openings being located below the capillary restriction member and the other pressure sensing opening being located adjacent but above said capillary restriction member, and means on the upper end of said double wall tube to permit the upper end of the sampling device to be connected in communicating relation to a differential pressure transducer and to a mass spectrometer, whereby the lung gases can be analyzed and the lung capacity determined.

7. The disposable gas sampling device as defined in claim 6 wherein said double wall tube comprises an elongate endotracheal tube having its lower end portion extending into the lower trachea of the human subject.

8. The disposable gas sampling device as defined in claim 6 wherein the double wall tube comprises a mouthpiece having a lower end portion extending into the oral cavity of the human subject.

9. The disposable gas sampling device as defined in claim 7 and means dividing the space between the inner and outer tubular elements into an elongate inflation passage, a tracheal sampling passage, and a tracheal return passage, a tracheal sample opening and a tracheal return opening in said inner tube communicating with said tracheal sample passage and a tracheal return passage, a pair of inflation openings in said outer tube, and a pair of inflatable balloon members secured to said outer tube element, each of said inflation openings communicating with one of said balloon members to permit inflation and deflation of the latter, said balloon members, when inflated, engaging the inner surface of the trachea of the human subject and cooperating therewith to define an annular tracheal sampling cell, said tracheal sampling opening and said tracheal return opening communicating with the tracheal sampling cell, means for selectively connecing said tracheal sampling and return passages to said mass spectrometer to permit tracheal tissue gases to be analyzed.

* * * * *